United States Patent [19]

Matthews et al.

[11] 4,372,857
[45] Feb. 8, 1983

[54] LIQUID ADSORPTION PROCESS AND APPARATUS

[75] Inventors: William G. Matthews, Bridgewater, N.J.; Jean-Paul Sicard, Putnam Valley; Richard A. Anderson, Katonah, both of N.Y.

[73] Assignee: Union Carbide Corporation, Danbury, Conn.

[21] Appl. No.: 240,860

[22] Filed: Mar. 5, 1981

[51] Int. Cl.³ .............................................. B01D 15/00
[52] U.S. Cl. ...................... 210/673; 210/677; 210/678; 210/679; 210/689
[58] Field of Search ............. 210/673, 677–679, 210/689, 284, 290, 335, 340; 568/840

[56] References Cited

U.S. PATENT DOCUMENTS

| | | | |
|---|---|---|---|
| 1,541,921 | 6/1925 | Caps | 210/284 |
| 2,666,741 | 1/1954 | McMullen | 210/290 |
| 2,985,589 | 5/1961 | Broughton et al. | 210/677 |
| 3,080,433 | 3/1963 | Hengstebeck | 260/669 |
| 3,161,488 | 12/1964 | Eastwood et al. | 55/30 |
| 3,385,787 | 5/1968 | Crits et al. | 210/673 |
| 3,436,839 | 4/1969 | Ellington | 34/80 |
| 3,517,817 | 6/1970 | Hitzel | 210/279 |
| 3,606,730 | 9/1971 | Clark et al. | 55/33 |
| 3,929,130 | 12/1975 | Hargest | 210/290 |
| 4,030,896 | 6/1977 | Wimber et al. | 55/33 |
| 4,233,038 | 11/1980 | Tao | 55/33 |

Primary Examiner—Ivars C. Cintins
Attorney, Agent, or Firm—Henry H. Gibson; Gerald L. Coon

[57] ABSTRACT

Adsorbate is removed from a liquid mixture using a vessel containing a side effluent exit port above a zone of adsorbent material and below a second zone of adsorbent material used to remove adsorbate from a reverse flow regenerating fluid.

15 Claims, 2 Drawing Figures

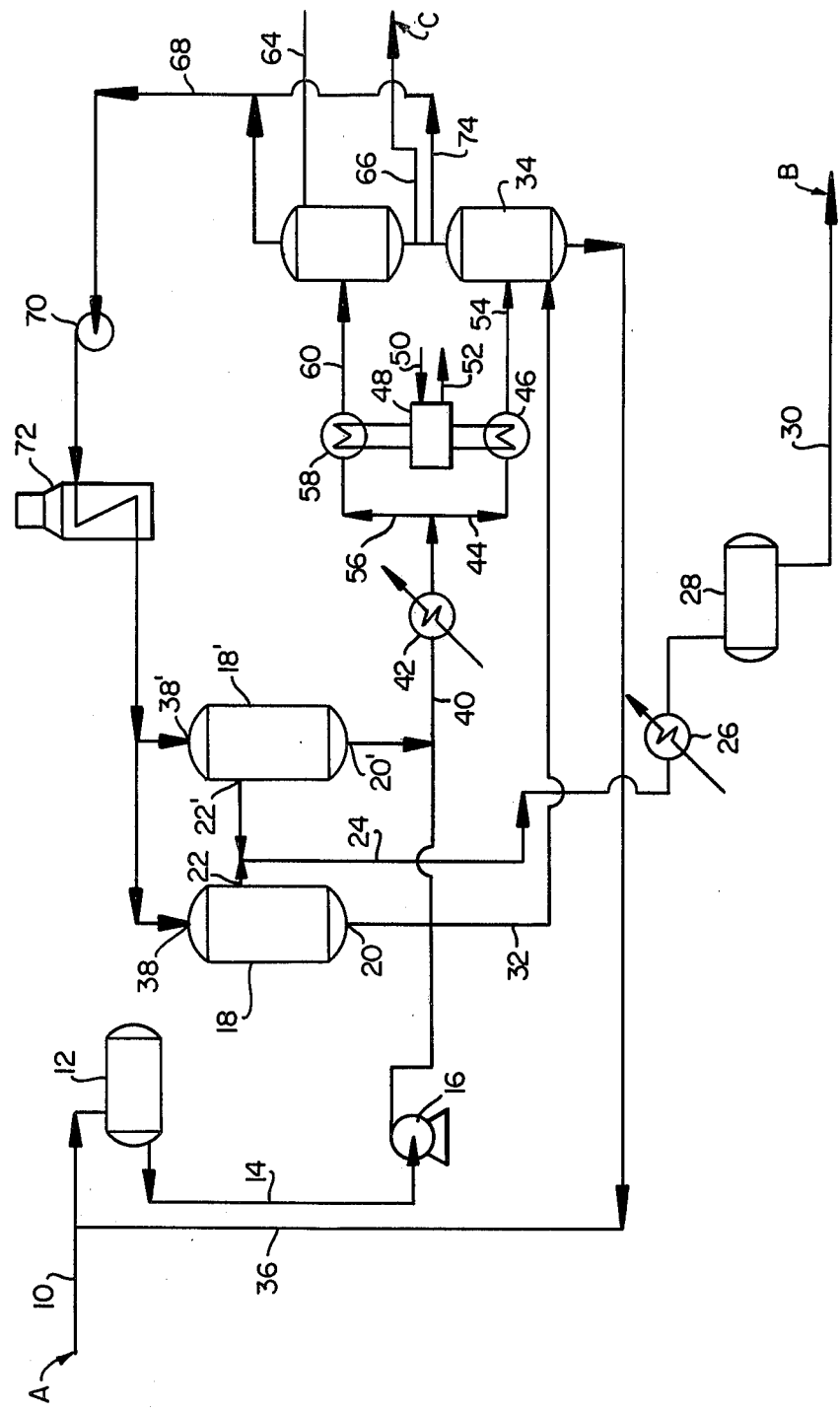

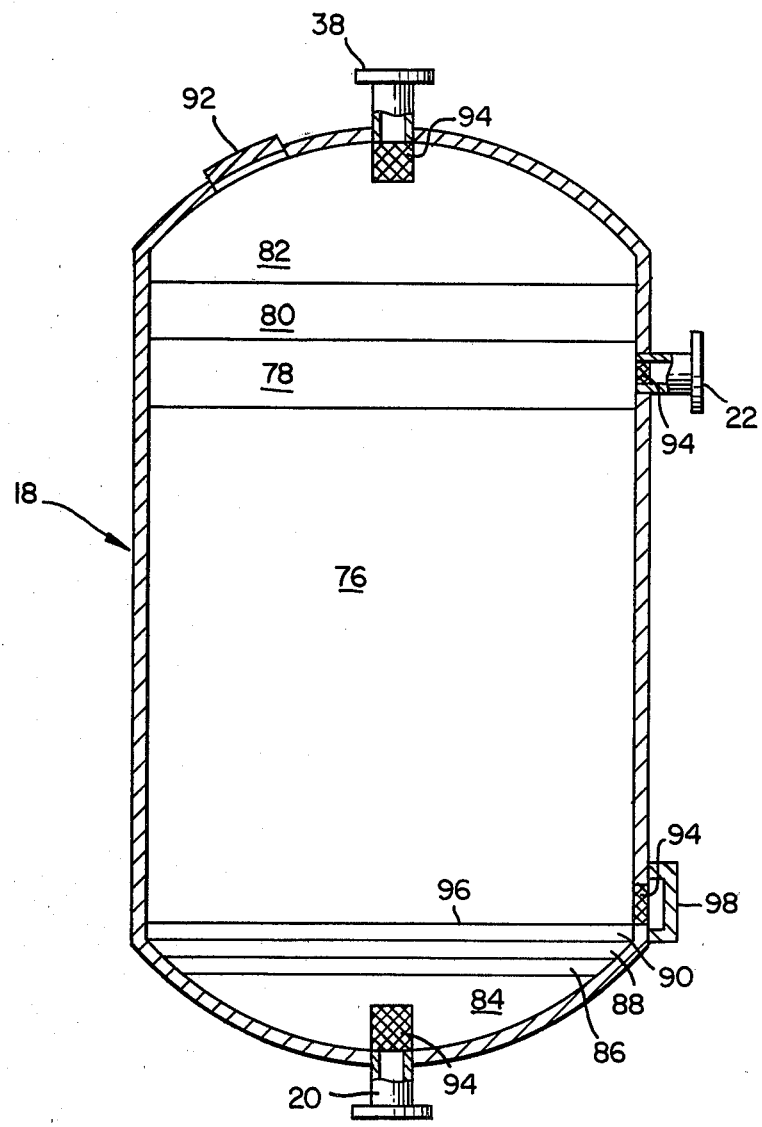

LIQUID ADSORPTION PROCESS AND APPARATUS

BACKGROUND OF THE INVENTION

1. Field of the Invention

This invention relates to the separation of an adsorbate component from a liquid mixture. More particularly, it relates to an improved process and apparatus for the bulk, liquid-phase absorptive dehydration of alkanol/water azeotropic compositions.

2. Description of the Prior Art

Large quantities of ethanol, i.e. ethyl alcohol, derived from fermentation and synthesis processes, are produced annually. Ethanol is important as a solvent or extractant in the manufacture of protective coatings, nitrocellulose, smokeless powder, cosmetics and pharmaceuticals. It is a raw material for the production of ethyl esters and chloroform. It can be oxidized to acetaldehyde to produce higher molecular-weight organic chemicals, and is an important intermediate in the production of vinegar, pharmaceuticals, dyes, detergents, polishes, photographic materials and lubricants.

Important industrial sources of ethanol from agricultural materials are fermentation products of sugars obtained from blackstrap molasses generated in sugarcane mills, starchy materials such as corn and potatoes, and sulfite waste liquor from wood pulp. Synthetic ethanol has been obtained from ethylene, which was derived from petroleum fractions and natural gas liquids. Ethylene was absorbed in sulfuric acid to yield ethyl sulfates which were hydrolyzed to crude ethyl alcohol and sulfuric acid. The alcohol was subsequently fractionated to produce 95% ethanol. One of the main commercially important synthetic processes now practiced is the direct hydration of ethylene over a phosphoric acid catalyst.

In the past, there occurred a gradual shift from fermentation-derived alcohol to synthetic materials as the principal feedstock. In the recent past, synthetic ethanol comprised a large portion of the total ethanol production. This was a consequence of economic factors such as the unavailability of molasses and relatively cheap ethylene. More recently, however, other factors, such as the shut down of ethyl sulfate process plants, sharp increases in petroleum feedstock costs, the revival of fermentation facilities and the availability of sugarcane-fermentation alcohol, have all acted to change the supply balance between the two industrial sources. This brought about an increase in the annual output of fermentation-based ethanol, including potable alcohol. This increase was attributed mainly to an increasing use of "gasohol," blend of 90% gasoline and 10% ethanol. For the same time period, synthetic ethanol production also expanded. Due in part to the increasing fuel shortage, national objectives have been made for increasing the annual production of fuel ethanol.

Fermentation-based ethanol as condensed from the distillation column is typically 95–95.6 weight-% alcohol, with the balance being mainly water. This mixture is described as "azeotropic," in that vapors boiling from the liquid have the same composition as the liquid. Therefore, it is not possible to achieve a higher concentration by ordinary distillation. In order to obtain anhydrous (99.9+%) ethanol, various extraction/distillation techniques have been tried in order to "break" this azeotrope. The most successful of these processes involves the use of benzene as a third component. This, however, is a costly and energy-intensive method and also involves a material of known toxicity. Chemical means of dehydrating the azeotrope are known, such as the use of calcium oxide, but this is not practical or economical on an industrial scale because of subsequent separation problems.

Adsorptive materials, such as molecular sieves, may be effectively used in processes for the adsorptive dehydration of an azeotropic mixture of ethanol and water as an alternative to distillation or other separation method. Molecular sieve adsorbents effect separations of liquid mixtures by virtue of an adsorptive preference for one or more of the mixture components. The preference can be based on molecular size, i.e. the ability of the preferred adsorbate to enter a pore system of the molecular sieve, to the exclusion of other molecular species. In such cases the preference is absolute. Preference can also be based on the polar character of the potential adsorbates or on their relative volatility. In general the more polar and the less volatile species are preferably, i.e. selectively, adsorbed. This latter condition is that which primarily occurs in adsorptive dehydration. The commercial application of molecular sieves to liquid drying is usually conducted in conventional multi-vessel equipment. Each vessel is operated alternately in dehydration, i.e. adsorption, and regeneration, i.e. desorption, stages. A typical application involves the following series of steps:

1. Feeding the azeotrope to be dehydrated to the vessel containing a layer or zone of adsorptive material, either in an upflow or downflow direction, for a predetermined time. Usually this time will be slightly less than the time required for breakthrough of the water into the effluent.

2. Draining the vessel of the bulk of the azeotrope contained in the void spaces within the zone of adsorbent material 3. Using a countercurrent, hot regeneration fluid to remove both any residual, void-azeotrope and the adsorbed water. Both of these will normally be collected by condensation and separated out from the regeneration fluid. The regeneration fluid is usually a relatively dry, non-adsorbable gas.

4. Returning the vessel to a temperature for carrying out adsorption by subsequently passing a cool regeneration fluid through the vessel.

5. Repeating the steps 1–4.

Another dehydration application, described in U.S. Pat. No. 3,080,433 (Hengstebeck), discloses a system for dehydrating olefin feedstock. In this procedure, however, the regeneration fluid is passed through the adsorption vessel in the same direction that the feedstock passes during dehydration. Other procedures used in adsorptive dehydration disclose the use of multiple layers of adsorptive materials within the vessel, such as in U.S. Pat. No. 3,161,488 (Eastwood et al).

It is also known in the art of liquid-phase separation using solid adsorbents contained in a vertical column, to have a purified effluent from an adsorption stage withdrawn at a point intermediate in the vessel. One such separation using molecular sieves as the adsorbent material is disclosed in U.S. Pat. No. 2,985,589 (Broughton et al). The procedure utilizes a simulated moving bed effected by means of a fluid-directing device referred to as "rotary valve." Withdrawal of the product is accomplished at selected (but periodically varying) locations in a column comprising a series of interconnected layers or sorption zones. There is also provided a timely, interacting flow of regeneration fluid into the column using the same valve. Other dehydration applications using vessels wherein fluids are introduced or withdrawn through intermediate points in the vessel, include those disclosed in U.S. Pat. No. 1,541,921 (Caps), U.S. Pat. No. 2,891,007 (Caskey et al.), U.S. Pat. No. 3,382,169 (Thompson), U.S. Pat. No. 3,517,817 (Hitzel) and U.S. Pat. No. 3,617,558 (Jones). The commercial, molecular sieve liquid-drying applications disclosed in the prior art, such as for propane and butane, may use either upflow or downflow operation in the adsorption stage.

The bulk, liquid-phase dehydration of an azeotropic mixture of ethanol and water using molecular sieve adsorption requires an extremely large quantity of regeneration fluid, due to the large molecular sieve adsorbent requirements for the large amount of water to be removed. To minimize the overall regeneration fluid requirements, a closed-loop regeneration cycle is required. The resulting process cycle consists of a liquid-phase adsorption stage in the upflow direction, followed by a draining step in the downflow direction, followed by a closed-loop regeneration stage. The latter stage may comprise initial heating steps and a cooling step, both in the downflow direction.

Problems have developed in this liquid-phase dehydration procedure. First, due to the large amount of adsorbate, i.e. water, to be removed, the treating rate is extremely slow. Since the mass-transfer rate is relatively good, the use of a conventional vessel design having effluent draw-off from the top of the vessel would require the mixture to "push" the effluent out of the vessel in a plug-flow manner. However, during the adsorption stage a certain amount of effluent is retained in the zone of adsorbent material due to the retention of effluent in macropores and voids in the adsorbent zones. Since an additional amount of mixture is required to "push" the effluent from the vessel, and to overcome the increased pressure due to the plugging effect at the top of vessel, there is a loss in the amount of effluent produced during each cycle of the adsorption stage due to a corresponding increase in the amount of mixture retained in the adsorbent. Second, since the adsorbent zone is being regenerated in a flow direction countercurrent to adsorption, any adsorbate or other adsorbable components contained in the cool regeneration fluid would be deposited in the adsorbent material adjacent the effluent end of the zone or bed during adsorption. If this adsorbate level is too high, enough adsorbate could be stripped by the product effluent during the next adsorption step to exceed the purity specifications for the effluent product. In many of the prior art liquid-phase dehydration applications the presence of such water in the product is nominal. However, in the requirements for making 99+% ethanol, for such applications as the preparation of gasohol, the presence of such water in the cool regeneration fluid is unacceptable. One solution for this problem would be to reduce the capacity of the cool regeneration fluid to retain adsorbate by lowering the temperature of the fluid to less than around 15° C. This, however, would require refrigeration of the regeneration fluid to ensure a low residual adsorbate level in the effluent. There is a need in the art, therefore, for improvements in the bulk, liquid-phase dehydration of such azeotropic mixtures.

It is an object of the invention to provide an improved process and apparatus for the liquid-phase adsorption of an adsorbate from a liquid mixture.

It is another object of the invention to provide an improved process and apparatus for the liquid-phase dehydration of a liquid mixture without effluent loss due to the retention effect during withdrawal of the effluent.

It is a further object of the invention to provide an improved process and apparatus for the liquid-phase dehydration of an alcohol/water azeotrope to produce a high purity effluent.

With these and other objects in mind, the invention is described in detail, with the novel features being particularly pointed out in the appended claims.

SUMMARY OF THE INVENTION

The invention includes a liquid adsorption apparatus comprising at least one vessel having:

1. a bottom wall having a first opening therein;
2. a top wall having a second opening therein;
3. sidewalls extending between said top and bottom walls and having an exit port therein closer to the top wall than to the bottom wall;
4. a first larger layer of adsorbent material in said vessel between the first opening and said exit port; and
5. a second smaller layer of adsorbent material in said vessel between the second opening and said exit port.

The invention also includes an absorption process for separating an adsorbate comprising at least one more preferably adsorbable component from a feedstock liquid mixture containing a non-adsorbate comprising at least one less preferably adsorbable component from said feedstock, which comprises:

1. providing in a first zone a first quantity of an absorbent material which preferentially adsorbs said adsorbate component of said mixture with respect to said non-adsorbate component;
2. providing in a second zone a second quantity of absorbent material;
3. providing a relatively non-adsorbing, fluid permeable material in a third zone in contact with said first and second zones;
4. removing said adsorbate from said mixture by the steps of: (a) flowing said feedstock mixture into said first zone; (b) contacting said mixture with said first quantity of adsorbent material thereby preferentially adsorbing said adsorbate component of said mixture in said first quantity of adsorbent material, producing a non-adsorbate effluent essentially free of said adsorbate; (c) discharging said non-adsorbate effluent through said third zone;
5. regenerating the adsorbent materials by: (a) substantially removing the non-adsorbed components of said mixture from said first and third zones; (b) introducing a regenerating fluid, comprising a major proportion of a non-adsorbable gas and a minor proportion of a molecular species strongly adsorbable by said adsorbent material, into said second zone in a direction countercurrent to the direction of feedstock flow in step 4 (a), thereby substantially removing said strongly adsorbable molecular species from said non-adsorbable gas into said second quantity of adsorbent material; (c) passing the non-adsorbable gas from said second zone countercurrently through said third zone and said first zone thereby desorbing adsorbate from said first zone of adsorbent material into the non-adsorbable gas; and (d) discharging the non-adsorbable gas containing the desorbed adsorbate from said first zone.

BRIEF DESCRIPTION OF THE DRAWING

The invention is hereinafter described with reference to the accompanying drawings in which:

FIG. 1 is a schematic flowsheet of an illustrative embodiment utilizing two adsorbent vessels in parallel.

FIG. 2 is a cross-sectional view of an apparatus for carrying out a preferred embodiment of the invention.

DETAILED DESCRIPTION OF THE INVENTION

The present invention will become apparent from the following detailed description thereof when considered together with the accompanying drawings which are set forth as being exemplary of preferred embodiments of the present invention and are not intended, in any way, to be limitative thereof.

Referring in detail to FIG. 1, there is shown a schematic diagram of a system for removing adsorbate from liquid mixture feedstock. The feedstock liquid mixture, identified as "A" in FIG. 1, is passed from a source (not shown) through line 10 to feed tank 12. The liquid mixture is sent from feed tank 12 through line 14 to a pump 16 and then passed into vessel 18 containing adsorbent material, through opening 20 at the base of the vessel. In passage up through vessel 18, adsorbate is removed from the liquid mixture by the adsorbent. Adsorbate free effluent is withdrawn at exit port 22. The effluent is passed through line 24 and sent through cooler 26 into a storage tank 28. The effluent product, identified as "B" in FIG. 1, can be withdrawn from storage tank 28 using line 30, for subsequent utilization of the effluent. The adsorption stage is continued for a time slightly less than the time required for any adsorbate to reach exit port 22.

After the adsorption stage is completed, a drain-down step is conducted wherein the liquid mixture retained in vessel 18 is withdrawn and passes through line 32 to a recycle tank 34. The liquid mixture retained in recycle tank 34 can be passed through line 36 to feed tank 12 for use in a subsequent adsorption stage.

During the preceding steps a closed-loop regeneration stage is carried out for the vessel 18', having an effluent exit port 22', subsequent to being drained of liquid mixture as described above. A regeneration fluid is introduced into vessel 18' through opening 38'. A corresponding opening 38 is provided in vessel 18 to be used when that vessel is undergoing regeneration. In a preferred embodiment, the regeneration fluid is introduced into vessel 18' in three steps.

In the first step, warm regenerating fluid, at a temperature of between 50° C. and 150° C., is passed through vessel 18'. The fluid, passing in a downflow direction, drives off the "sponge liquid," i.e. the liquid mixture which is caught in macropores of the adsorbent and in voids between the adsorbent material. The spent warm regeneration fluid is withdrawn from vessel 18' through opening 20' and passes through line 40 to a cooler 42. Mixture is recovered from the warm regeneration step by passing the spent regeneration fluid through line 44 into a chiller 46, which is part of a refrigeration unit 48. A heat exchange fluid, such as cold water, is introduced into the refrigeration unit through line 50 and withdrawn through line 52. The recovered mixture, which contains some adsorbate, is passed through line 54 to recycle vessel 34, where it may be recycled for use in a subsequent adsorption stage.

In the second step, hot regeneration fluid, at a temperature of over 200° C., is passed into vessel 18. During this step the remaining adsorbate is desorbed from the adsorbent. The spend hot regeneration fluid is withdrawn from vessel 18' through opening 20', and passes through line 40 into cooler 42. The fluid then passes through line 56 to a second chiller 58, and is then sent through line 60 to an absorbate knock-out tank 62. The adsorbate is removed from the regeneration fluid in knock-out tank 62 by passing the fluid through an absorbate-removing zone provided with a spray/quench of water drawn from line 64. The adsorbate, identified as "C" in FIG. 1, then can be removed from the system through line 66. The regeneration fluid passes from knock-out tank 62 through line 68 for reuse during the same or a subsequent regeneration stage. The regeneration fluid is recycled by being passed through blower 70 to heater 72 which is used to adjust the temperature of the fluid during the regeneration stage. Spent regeneration fluid may also be recycled from recycle vessel 34 through line 74 for use in a subsequent regeneration stage.

In the third step, cool regeneration fluid at a temperature of around 30° C. to 50° C. is passed through vessel 18'. This step is required as a cool-down period to bring down the temperature of the molecular sieve adsorbent in the vessel. At the end of the third step, vessel 18' is ready for another adsorption stage.

Make-up regeneration fluid is supplied to the regeneration system as required from a suitable supply source, using a conventional combination of purge tanks, compressors and vents (not shown). The fluid should be essentially free of impurities such as molecular species which may be strongly adsorbable by the first zone of adsorbent material. The impurities in the regeneration fluid could be adsorbed or retained by the adsorbent material thereby decreasing its efficacy. The impurities could also be retained in the effluent, thereby decreasing the quality of the effluent.

In a preferred embodiment, as shown in FIG. 2, the adsorber vessel 18 (and 18') has cylindrical side walls and is provided with a larger layer or zone 76 of adsorbent material. The adsorbent layer 76 can consist of any material which preferentially and selectively adsorbs an adsorbate comprising at least one more preferable adsorbable component, such as water, from a feedstock liquid mixture containing a non-adsorbate comprising at least one less preferable adsorbable component, such as ethanol. Exit port 22 is located in the side wall of vessel 18, just above larger adsorbent layer 76. A section of non-adsorbing, fluid permeable material may be provided adjacent to exit port 22. In a preferred embodiment, the non-adsorbing, fluid permeable material takes the form of a layer 78 covering larger adsorbent layer 76. The non-absorbing, fluid permeable layer 78 may be made up of an assembly of one or more suitable perforated or slotted plates, grids or other suitable spacing means known in the art. In a preferred embodiment, the non-adsorbing, fluid permeable layer 78 is made up of $\frac{1}{8}$ inch ceramic balls.

A second, smaller layer of adsorbent material 80 is positioned between exit port 22 and opening 38 in the top wall of vessel 18. Smaller adsorbent layer 80 may be made of any material which removes an adsorbate or other strongly sorbable component from a regenerating fluid entering vessel 18 through opening 38.

Layers of fluid permeable material 82, 84, 86, 88 and 90 may also be provided above and below adsorbent layers 76 and 80. These layers may be made up of the same or similar materials as those described for non-absorbing, fluid permeable layer 78. In a preferred embodiment, non-adsorbing, fluid permeable layer 82, positioned between adsorbent layer 80 and opening 38, is made up of one inch ceramic balls. Likewise, non-adsorbing, fluid permeable layer 84, adjacent opening 20 in the bottom wall of vessel 18, may be made up of one inch ceramic balls. Non-adsorbing, fluid permeable layers 86, 88, and 90, positioned between non-adsorbing, fluid permeable layer 84 and larger adsorbent layer 76, may be made up of ½ inch, ¼ inch and ⅛ inch ceramic balls respectively. These non-adsorbing, fluid permeable layers, used in accordance with conventional adsorber practice, reduce adsorbent attrition caused by the disruption of adsorbent layers 76 and 80 when fluid material enters through openings 20 or 38 and impinges upon the adsorbent layer surfaces.

A loading manhole 92 may be provided in the top wall of vessel 18 through which the adsorbent material and the non-adsorbing, fluid permeable material may be added to vessel 18. The vessel openings 20, 22 and 38 may be provided with screens 94 which prohibit the loss of the adsorbent and fluid permeable materials through the vessel openings, while permitting the ingress and egress of the fluids through the openings. A floating screen 96 may also be provided at the base of layer 76. Vessel 18 may also be provided with external insulation (not shown).

EXAMPLE

In operation, the feedstock comprises a liquid mixture of an ethanol/water azeotrope typically supplied from a beer-fermentation still and containing 92.42 weight-percent ethanol, i.e. around "190 proof," and 7.58 weight-percent water. The azeotrope is typically at a temperature of around 25° C. and a flow rate of 2280 gallons per hour(GPH) The alcohol/water azeotropic mixture is introduced into vessel 18 through opening 20 at, e.g., a pressure of 50 pounds per square inch gauge (psig). The water is removed from the mixture by introducing the mixture into the first zone or layer 76 of activated adsorbent material. The adsorbent material is preferably a molecular sieve, such as Type 3A Molecular Sieve which is the designation for a material sold by Union Carbide Corporation. In a preferred embodiment, the larger adsorbent layer 76 is made up of around 63,000 pounds of activated Type 3A Molecular Sieve. In this embodiment, the larger adsorbent layer 76 has a diameter of around 12 feet, and a height of around 14 feet. The water is preferentially adsorbed from the mixture into the adsorbent material thereby producing an essentially water-free effluent of greater than 99% ethanol. This adsorption stage usually requires around 8 hours. The ethanol effluent, continuing in an upflow direction, is discharged from the vessel at e.g. 1345 GPH, through exit port 22, after passing through non-adsorbing, fluid-permeable layer 78. This effluent is 199-proof ethanol containing 0.08 weight-percent water or less. This solves the first of the above-described problems with the prior art, by not requiring the liquid mixture to "push" the ethanol out of the top of the vessel. Prior to the time when water would begin to exit through port 22, i.e. when larger adsorbent layer 76 has become saturated with water, the introduction of the liquid mixture into vessel 18 is stopped.

A regeneration phase is then conducted by first removing the liquid mixture from the vessel by draining the liquid from adsorbent layer or zone 76 through opening 20, or in a preferred embodiment through dump port 98, for usually around 0.5 hours duration. A regeneration fluid comprising a major proportion of non-adsorbable gas, such as carbon dioxide ($CO_2$) gas, nitrogen or hydrocarbons such as hexane is introduced into vessel 18 through opening 38. $CO_2$ generated from a fermentation process may contain significant qualities of ethanol, hydrogen sulfide and sulfur dioxide. These impurities, if present, should all be in the parts per million per unit volume (ppmv) range. In addition, the $CO_2$ should not contain any oxygen. In a preferred embodiment, the regeneration fluid for the warm, hot and cool steps is 100% $CO_2$. Gases other than $CO_2$ can be utilized so long as they are inert to the adsorbent material, in that they must exhibit a low propensity for being adsorbed or retained in the adsorbent. In the first regeneration step, warm $CO_2$ gas removes most of the mixture retained in vessel 18. The procedure requires passing the $CO_2$ gas through the vessel, usually for around 1.9 hours, at a flow rate of 28 million standard cubic feet per day (MMSCFD). In the second regeneration step, hot $CO_2$ gas removes the water from vessel 18, usually for a period of around 2.2 hours at the same flow rate of 28 MMSCFD, by desorbing the water component away from the layers 76 and 80 of adsorbent materials and into the $CO_2$ gas. In the third step, a cool $CO_2$ gas is introduced into vessel 18, usually for around 0.7 hours, to cool the molecular sieve in the vessel to an operating temperature sufficient for conducting the next adsorption phase. The gas temperature is preferably around 35° C., and is introduced at the same pressure and flow rate as in the two previous steps. In this third step, water which may have been retained in the recycled carbon dioxide ($CO_2$) gas, or any other strongly-adsorbable molecular species in the fluid, is selectively adsorbed from the regeneration fluid by its passage through adsorbent layer or zone 80. In a preferred embodiment, smaller adsorbent layer 80 is made up of an activated molecular sieve such as Type 3A or 4A Molecular Sieves. The second problem described above is therefore solved by keeping this water or other adsorbable species above the point from which ethanol is removed from the vessel. The potential for back-mixing is thereby removed since the removed components are not stripped from the adsorbent zone or layer 80 by the ethanol effluent. Typically, the residual water loading on the molecular sieve adsorbent following regeneration as described above is, on the average, about 6 weight-percent.

Additional vessels, such as vessel 18', may be provided in parallel with vessel 18 such that the various cyclical steps of an upflow adsorption phase, a drain-down removal of liquid mixture, a downflow warm regeneration step, a downflow hot regeneration step and a downflow, cool-down regeneration step may be conducted in a complimentary relationship among the vessels.

As stated hereinabove, molecular sieve adsorbents in general effect separations by virtue of certain adsorptive preferences. In order for the pore system of the molecular sieve material to be available to potential adsorbates, such sieve must first be suitably dehydrated at least partly, preferably to a residual water content of less than 1 weight-percent, i.e., by removal of intracrystalline "zeolitic" water or water of hydration according to methods well known in the art. This treatment creates an activated condition for subsequent adsorption.

Accordingly, the molecular sieve adsorbent materials referred to hereinabove are initially in a suitably activated condition.

What is claimed is:

1. An adsorption process for separating an adsorbate comprising at least one more preferably adsorbable component from a feedstock liquid mixture containing a non-adsorbate comprising at least one less preferably adsorbable component from said feedstock, which comprises:
   (i) providing in a first zone a first quantity of adsorbent material which preferentially adsorbs said adsorbate component of said mixture with respect to said non-adsorbate component;
   (ii) providing in a second zone a second quantity of adsorbent material;
   (iii) providing a relatively non-adsorbing, fluid permeable material in a third zone in contact with said first and second zones;
   (iv) removing said adsorbate from said mixture by the steps of:
      (a) flowing said feedstock mixture into said first zone;
      (b) contacting said mixture with said first quantity of adsorbent material thereby preferentially adsorbing said adsorbate component of said mixture in said first quantity of adsorbent material, producing a non-adsorbate effluent essentially free of said adsorbate;
      (c) discharging said non-adsorbate effluent through said third zone;
   (v) regenerating the adsorbent materials
      (a) substantially removing the non-adsorbed components of said mixture from said first and third zones;
      (b) introducing a regenerating fluid, comprising a major proportion of a non-adsorbable gas and a minor proportion of a molecular species strongly adsorbable by said adsorbent material, into said second zone in a direction countercurrent to the direction of feedstock flow in step iv(a) thereby substantially removing said strongly adsorbable molecular species from said non-adsorbable gas into said second quantity of adsorbent material;
      (c) passing the non-adsorbable gas from said second zone countercurrently through said third zone and said first zone thereby desorbing said adsorbate from said first zone of adsorbent material into the non-adsorbable gas; and
      (d) discharging the non-adsorbable gas containing the desorbed adsorbate from said first zone.

2. The process according to claim 1 whereby said molecular species is the adsorbate comprising at least one more preferably adsorbable component of said feedstock mixture.

3. The process of claim 1 whereby said third zone extends entirely between said first and second zones.

4. The process according to claim 1 whereby two or more series of zones are provided in parallel so that at least one series of zones is undergoing a removal stage while at least one other series of zones is undergoing a regeneration stage.

5. The process according to claim 1 whereby the regenerating fluid is introduced in several steps of:
   (a) passing warm regenerating fluid at a temperature of between 50° C. and 150° C. through the zones;
   (b) passing hot regenerating fluid at a temperature of over 200° C. through the zones; and
   (c) passing cool regenerating fluid at a temperature of around 30° C. to 50° C. through the zones.

6. The process according to claim 1 whereby the liquid mixture removed from said first zone is recycled for use in a subsequent removal stage.

7. The process according to claim 1 whereby any mixture recovered by the regenerating fluid is recycled for use in a subsequent removal stage.

8. The process according to claim 1 or 5 whereby the adsorbate is removed from the regenerating fluid after use and the regenerating fluid is then recycled to the regeneration stage.

9. The process according to claim 1 whereby the regenerating fluid comprises a major proportion of a non-adsorbable gas.

10. The process according to claim 9 whereby the non-adsorbable gas is carbon dioxide gas.

11. The process according to claim 1 whereby the liquid mixture is an alcohol/water azeotrope.

12. The process according to claim 11 whereby the adsorbate is water.

13. The process according to claim 11 whereby the alcohol is ethanol.

14. The process according to claim 1 whereby the first quantity of adsorbent material is larger than the second quantity of adsorbent material.

15. The process according to claim 1 wherein said process is carried out in a liquid adsorption apparatus comprising at least one vessel having:
   (a) a bottom wall having a first opening therein;
   (b) a top wall having a second opening therein;
   (c) side walls extending between said bottom and top walls and having an exit port therein closer to the top wall than to the bottom wall;
   (d) a first larger layer of adsorbent material in said vessel between the first opening and said exit port; and
   (e) a second smaller layer of adsorbent material in said vessel between the second opening and said exit port.

* * * * *